(12) United States Patent
Qazi et al.

(10) Patent No.: US 7,041,482 B2
(45) Date of Patent: May 9, 2006

(54) **OLIGONUCLEOTIDE PRIMERS HAVING SEQ ID NOS. 1 TO 21 AND A PROCESS FOR DETECTION OF PARASITE *SALMONELLA* USING OLIGONUCLEOTIDE PRIMERS**

(75) Inventors: Ghulam Nabi Qazi, Jammu (IN); Vijeshwar Verma, Jammu (IN); Syed Riyaz-Ul-Hassan, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 379 days.

(21) Appl. No.: 10/440,211

(22) Filed: May 15, 2003

(65) Prior Publication Data

US 2004/0229227 A1    Nov. 18, 2004

(51) Int. Cl.
*C12P 19/34*    (2006.01)

(52) U.S. Cl. ..................................... 435/91.2
(58) Field of Classification Search ............... 435/91.2

See application file for complete search history.

(56) References Cited

OTHER PUBLICATIONS

Carli et al. (2001) "Detection of *Salmonellae* in chicken feces by a combination of tetrathionate broth enrichment, capillary PCR, and capillary gel electrophoresis", *Journal of Clinical Microbiology*, 39: 1871-1876.

Ferretti et al. (2001) "Twelve-hour PCR-based method for detection of *Salmonella* spp. in food", *Applied and Environmental Microbiology*, 67: 977-978.

Mead et al. (1999) "Food-related illness and death in the United States", *Emerging Infectious Diseases*, 5: 607-625.

*Primary Examiner*—Mark Navarro
(74) *Attorney, Agent, or Firm*—Baker Botts LLP (57) ABSTRACT

The present invention relates to oligonucleotide primers having SEQ ID NOs. 1 to 21 specific for *Salmonella* enterotoxin gene (stn) gene, useful for rapid and specific screening of *Salmonella*. The present invention relates to a process for the rapid and specific detection of *Salmonella* enterotoxin gene (stn) gene in a subject for the presence of parasite *Salmonella* using oligonucleotide primers having SEQ ID NOs. 1 to 21 for Polymerase Chain Reaction (PCR), said process comprising the steps of preparing a DNA template, amplifying the template using the primers by PCR, running the PCR products on gel, and detecting the *Salmonella*.

16 Claims, 3 Drawing Sheets

SEQUENCE LISTING

<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 1
gaagcagcgc ctgtaaaatc                                              20

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 2
tggctgtggt gcaaaatatc                                              20

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 3
gccaccagct tttctttacg 20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 4
acgaaccagc gaaacaaact 20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 5
ggtcaaaatc cagcggttta 20

<210> SEQ ID NO 6
<211> LENGTH: 18
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 6
ttgctgctaa cggcgaga 18

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 7
gccggctttc aacgcctcta c 21

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 8
gaccaaagct gacgggacag                                                    20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 9
acgcctctac cgccgtttcc                                                    20

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 10
cgaccaaagc tgacgggaca g                                                  21

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 11
cgtttccacg ctggaaaatg c                                                  21

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 12
gccggctttc aacgcctcta c                                                  21

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 13
catggcggcg cgattaagg                                                     19

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 14
aatcggaatg gcgggattga g                                              21

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 15
tgccgttcat aatcaaaatc g                                              21

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 16
gattttacag gcgctgcttc                                                20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 17
ggtcaaaatc cagcggttta                                                20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 18
gctcaggtgc gtgagaaagt                                                20

<210> SEQ ID NO 19
<211> LENGTH: 20
<212> TYPE: DNA
<213> ORGANISM: Artificial Sequence
<220> FEATURE:
<223> OTHER INFORMATION: Oligonucleotide primer specific to Salmonella enterotoxin stn gene

<400> SEQUENCE: 19
gttcgagcaa ttcgcttacc                                                20

<210> SEQ ID NO 20

```
<211> LENGTH: 20
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 20
gcttgatgca atgaagcgta                                              20

<210> SEQ ID NO 21
<211> LENGTH: 20
<212> TYPE: DNA
<213> ORGANISM: Artificial Sequence
<220> FEATURE:
<223> OTHER INFORMATION: Oligonucleotide primer specific to Salmonella
      enterotoxin stn gene

<400> SEQUENCE: 21
ttcccgctat cggtaacagt                                              20
```

OLIGONUCLEOTIDE PRIMERS HAVING SEQ ID NOS. 1 TO 21 AND A PROCESS FOR DETECTION OF PARASITE *SALMONELLA* USING OLIGONUCLEOTIDE PRIMERS

The present invention relates to oligonucleotide primers comprising SEQ ID NOs. 1 to 21, specific for *Salmonella* enterotoxin gene (stn) gene, useful for rapid and specific screening of *Salmonella*. The present invention also relates to a process for the rapid and specific detection of *Salmonella* enterotoxin gene (stn) gene in a subject for the presence of parasite *Salmonella* using oligonucleotide primers comprising SEQ ID NOs. 1 to 21 for Polymerase Chain Reaction (PCR), said process comprising steps of preparing DNA template of the gene, amplifying the template using the primers by PCR, running the PCR products on gel, and detecting the parasite.

BACKGROUND OF THE INVENTION

*Salmonella* species are facultative, intracellular parasites that invade the mucous membrane of the epithelial cells and are transmitted to humans mainly through water, meat, eggs and poultry products. *Salmonella* infection is the most frequent food-borne gastrointestinal disease transmitted from animals to humans. Typhoid fever still remains endemic in many developing countries and non-typhoidal salmonellosis also is a major food-borne disease worldwide and is estimated to be responsible for the deaths of more than 500 people each year, with costs of $1 billion to $1.5 billion annually in the United States alone (Threlfall 1996; Mead et al. "Food-related illness and death in the United States," Emerg Infect Dis., 1999,5:607–25.) These figures in India are not fully documented but expected to be much higher. To prevent *Salmonella* infection, good monitoring and screening programs are required. Detection of *Salmonella* by conventional bacteriological methods are time consuming and usually requires 5 to days. Therefore, efforts have been made by many workers to reduce time required and to increase the sensitivity of the methods to detect *Salmonella* (Notermans et al. 1997; Ferretti et al., "Twelve-hour PCR-based method for detection of *Salmonella* spp. in food," Appl Environ Microbiol., 2001, 67:977–8; Carli et al., "Detection of salmonellae in chicken feces by a combination of tetrathionate broth enrichment, capillary PCR, and capillary gel electrophoresis," J Clin Microbiol., 2001, 39:1871–6).

Increased public awareness of the health related and economic impact of food-borne contamination and illness has resulted in greater efforts to develop more sensitive methods of pathogenic detection and identification. Advances in molecular biology technology, particularly the polymerase chain reaction (PCR), have allowed more reliable microbial identification and surveillance. PCR has also become a valuable tool for investigating food-borne outbreaks and identification of etiological agents responsible for the microbial epidemics. PCR techniques have provided increased sensitivity, allowed more rapid processing times and enhanced the detection of bacterial pathogens. In addition to analysis of foods, PCR has also been successfully applied for the detection and identification of pathogenic microorganisms in clinical and environmental samples (Simon 1999; White, 1992).

Enterotoxigenicity has been recognized as one of the distinct pathological attributes of diarrhea inducing bacteria. *Salmonella* serotypes, which are known for their association with gastroenteritis and diarrhea in humans and animals, have also been shown to produce enterotoxin. The stn gene is located at approximately 89 minutes on the *Salmonella typhimurium* chromosome and the presence of an intact stn gene contributes significantly to the overall virulence of *Salmonella*. The present invention relates to the use of stn gene as a detection marker for *Salmonella*.

SUMMARY OF THE INVENTION

The present invention relates to a PCR-based method of identifying *Salmonella* species using novel oligonucleotide primers for rapid and specific screening for the parasite from various sources. The oligonucleotide primers of the present invention are specific for the *Salmonella* enterotoxin gene (stn) gene. The present invention relates to a process for the detection of the parasite *Salmonella* using oligonucleotide primers specific for the *Salmonella* enterotoxin gene (stn) gene. The process comprises the steps of preparing DNA template from a sample, amplifying the PCR products using the oligonucleotide primers of the present invention, running the PCR products on an agarose gel, and detecting the parasite. The present invention also provides for novel oligonucleotide primers specific for the stn gene having SEQ ID NOs: 1–21.

The main object of the present invention is to develop primers for the detection of parasite *Salmonella*.

Another main object of the present invention is to develop a rapid and efficient process for the detection of parasite *Salmonella*.

Yet another main object of the present invention is to develop a process for the detection of parasite *Salmonella* from food, biological samples, etc.

DETAILED DESCRIPTION OF THE INVENTION

The present invention provides for oligonucleotide primers having SEQ ID NOs. 1 to 21 are specific for *Salmonella* enterotoxin gene (stn) gene. The oligonucleotide primers having SEQ ID NOs. 1 to 21 are useful for rapid and specific screening of *Salmonella*.

The oligonucleotide primer sets 1–4 are listed in Table 1 below.

TABLE 1

Oligonucleotide primer sets 1-4 for stn gene

| | Primer name | Sequences | SEQ ID NO. |
|---|---|---|---|
| Set 1 | QVR133 | 5' GAAGCAGCGCCTGTAAAATC 3' | 1 |
| | QVR134 | 5' TGGCTGTGGTGCAAAATATC 3' | 2 |
| Set 2 | QVR135 | 5' GCCACCAGCTTTTCTTTACG 3' | 3 |
| | QVR136 | 5' ACGAACCAGCGAAACAAACT 3' | 4 |
| Set 3 | QVR137 | 5' GGTCAAAATCCAGCGGTTTA 3' | 5 |
| | QVR138 | 5' TTGCTGCTAACGGCGAGA 3' | 6 |
| Set 4 | QVR139 | 5' GCCGGCTTTCAACGCCTCTAC 3' | 7 |
| | QVR140 | 5' GACCAAAGCTGACGGGACAG 3' | 8 |

Table 2 lists additional oligonucleotide primers of the present invention useful for the detection of the stn gene.

TABLE 2

Oligonucleotide primers for stn gene

| Sequences | SEQ ID NO. |
|---|---|
| 5' ACGCCTCTACCGCCGTTTCC 3' | 9 |
| 5' CGACCAAAGCTGACGGGACAG 3' | 10 |
| 5' CGTTTCCACGCTGGAAAATGC 3' | 11 |
| 5' GCCGGCTTTCAACGCCTCTAC 3' | 12 |
| 5' CATGGCGGCGCGATTAAGG 3' | 13 |
| 5' AATCGGAATGGCGGGATTGAG 3' | 14 |
| 5' TGCCGTTCATAATCAAAATCG 3' | 15 |
| 5' GATTTTACAGGCGCTGCTTC 3' | 16 |
| 5' GGTCAAAATCCAGCGGTTTA 3' | 17 |
| 5' GCTCAGGTGCGTGAGAAAGT 3' | 18 |
| 5' GTTCGAGCAATTCGCTTACC 3' | 19 |
| 5' GCTTGATGCAATGAAGCGTA 3' | 20 |
| 5' TTCCCGCTATCGGTAACAGT 3' | 21 |

According to the present invention, a PCR primer, or oligonucleotide primer, is an oligonucleotide capable of specific hybridization under particular PCR conditions to a region of the template DNA, which has a sequence which is substantially complementary to the primer sequence, and is adapted to prime the extension of DNA during PCR. A complementary sequence is capable of forming Watson-Crick bonds with its complement, in which adenine pairs with thymine or guanine pairs with cytosine. Each primer is typically used as a member of a primer pair, including a 5' upstream primer that hybridizes with the 5' end of the template DNA to be amplified and a 3' downstream primer that hybridizes with the complement of the 3' end of the template DNA to be amplified.

The present invention also relates to a method for the rapid and specific detection one or more *Salmonella* cells in a sample using oligonucleotide primers selected from the group consisting of SEQ ID NOs. 1 to 21. The process comprising preparing a DNA template from the sample, amplifying the template with the oligonucleotide primers using polymerase chain reaction (PCR) to amplify PCR products, running the PCR products on an agarose gel, and detecting the *Salmonella*.

The stn gene was sequenced from several serotypes of *Salmonella* and the sequence was found to be conserved. A PCR based protocol for the detection of *Salmonella* has been developed by using specific primers based on *Salmonella* enterotoxin gene (stn). These primers and the PCR protocols have been designed and are being reported herein.

Figure 1:
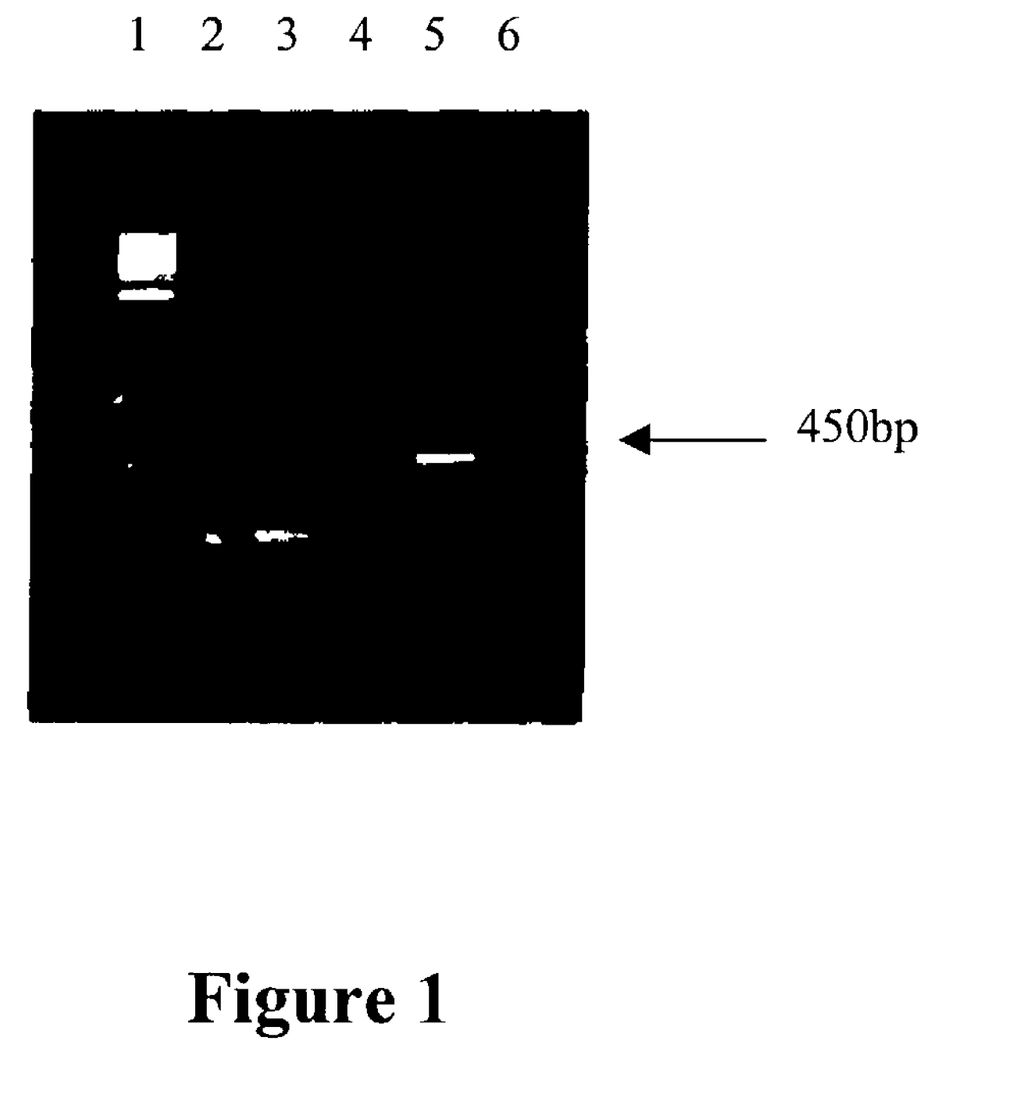
FIG. 1 is a 1% agarose electrophoretic gel showing with PCR products from reactions using oligonucleotide primers specific for the stn gene. PCR products were amplified using primers, QVR133 and QVR134 (Lane 2); QVR135 and QVR136 (Lane 3); QVR137 and QVR138 (Lane 4); QVR139 and QVR140 (Lane 5); QVR139 and QVR140 (Lane 6: Negative control)

In an embodiment of the present invention, primer set 1, listed on Table 1 and comprising SEQ ID NOs. 1 and 2, generate PCR products of approximately 200 bp as shown in FIG. 1 of the Examples section.

In another embodiment of the present invention, primer set 2, listed on Table 1 and comprising SEQ ID NOs. 3 and 4 generates PCR products of approximately 207 bp as shown in FIG. 1 of the Examples section.

In still another embodiment of the present invention, primer set 3, listed on Table 1 and comprising SEQ ID NOs. 5 and 6, generates PCR products of approximately 1318 bp as shown in FIG. 1 of the Examples section.

In still another embodiment of the present invention, primer set 4, listed on Table 1 and comprising SEQ ID NOs. 7 and 8, generates PCR products of approximately 450 bp as shown in FIG. 1 of the Examples section.

PCR amplification is conducted according to conventional procedures in the art. Preferably, the PCR method of the present invention includes the use of 1 μg to 10 μg of template DNA, a thermostable DNA polymerase, and oligonucleotide primers in the range of 1 pM to 100 pM for each primer. Each PCR is overlayed with mineral oil or the like to prevent evaporation of the reaction mix during cycling. PCR cycling is preferably run under the following conditions: initial denaturation at a temperature of 93° C. to 97° C. for 30 sec. to 7 min, followed by 23 to 50 cycles of 93° C. to 97° C. for 3 sec. to 2 min for denaturation, 50° C. to 67° C. for 10 sec to 2 min. for annealing, 70° C. to 75° C. for 10 sec. to 2 min for extension, followed by final extension at 70° C. to 75° C. for 2 min. to 10 min.

The PCR products may be visualized on an agarose gel of concentration ranging from 0.3% to 2.7%.

In an embodiment of the invention, the oligonucleotide primers are use in a nested PCR reaction. Nested PCR is a two, or more, stage PCR reaction in which the first stage requires the use of a primer set which flank and amplify a particular outer DNA segment, followed by a second stage in which a second inner primers set is used to amplify a smaller region of nucleic acid which is contained within the first amplified DNA segment. The nested PCR is a sensitive method of ensuring the accurate detection of desired sequences.

In an embodiment of the present invention, the DNA is prepared from a pure culture of *Salmonella*. In an alternative embodiment of the invention, the DNA is prepared from various sources, including but not limited to water, food and clinical samples, such as blood. The clinical samples may be obtained from humans or animals.

In an alternative embodiment of the invention, the samples used for the preparation of the DNA template in the PCR reaction are enriched to promote the growth of *Salmonella* and/or other microflora in blood samples. Preferably, an amount of the sample can be inoculated into a culture medium and incubated to amplify the population of *Salmonella* in the culture to facilitate detection. Chromosomal DNA may be isolated by any known method including preparation of heat shock lysate.

In still another embodiment of the present invention, wherein the said process can be used as quality control of water and diagnosis of bacterium *Salmonella*.

The present invention provides for oligonucleotide primers and a rapid method for the detection of *Salmonella* wherein all types of serotypes (FIG. 3) of *Salmonella* could be detected from varied sources such as food, blood (FIG. 2) and water samples with or without enrichment as less as 1 cell per ml or per g primers and a rapid method for the detection of *Salmonella* wherein all types of serotypes of *Salmonella* could be detected from varied sources containing 1 cell per 25 ml or 25 g of sample with or without enrichment.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention Materials and Methods DNA isolation for PCR: The cell pellet from 1 ml of the liquid culture or a single colony on the agar medium was suspended in 100 µl of sterilized Millipore water and incubated in a dry bath at 100° C. for 5 min. The mixture was immediately transferred to ice bath and left for 3 min. The resultant cell lysate was centrifuged at 7000 rpm for 3 min. and 2 µl of the supernatant was directly used in a 20 µl PCR reaction.

Figure 2:
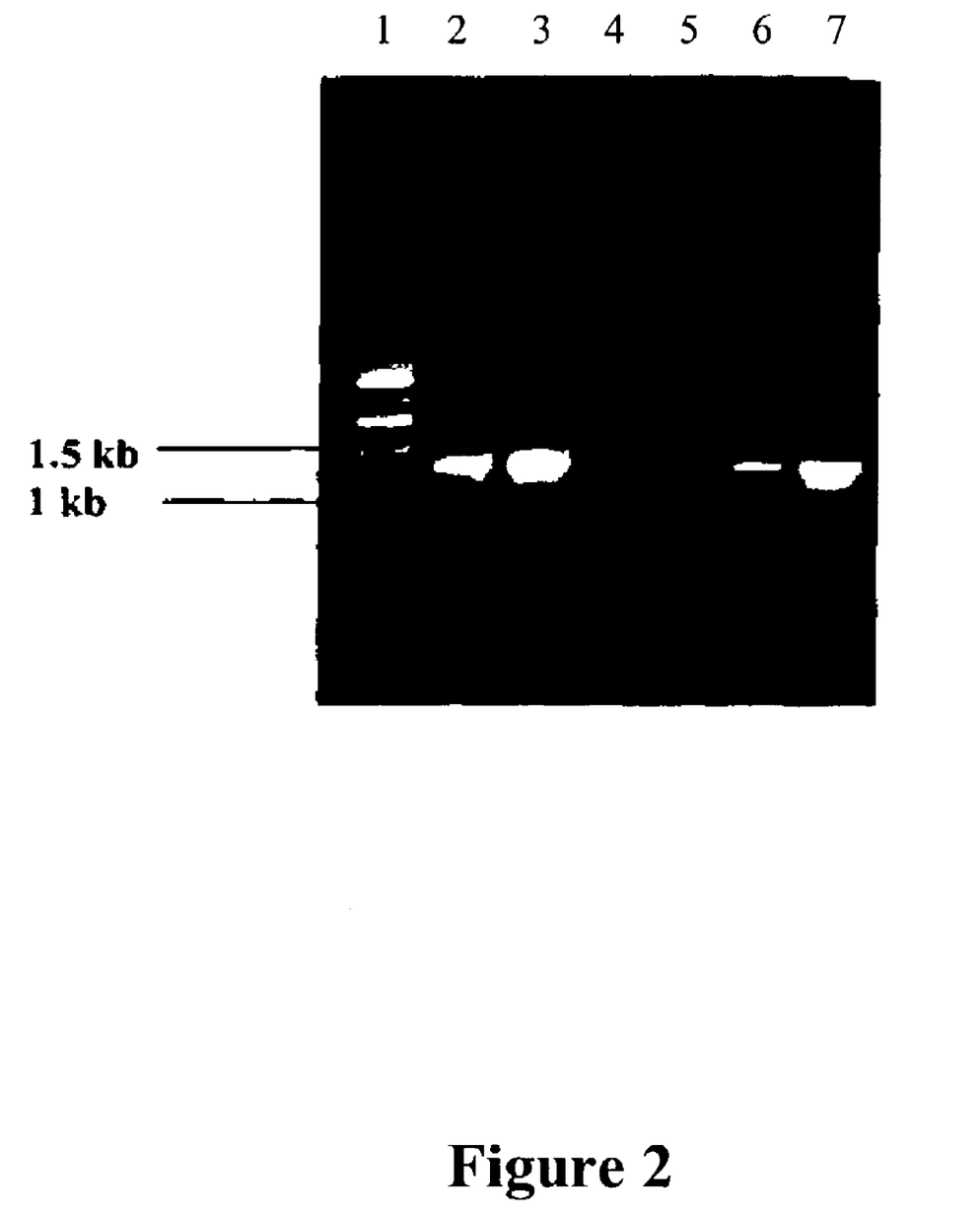
FIG. 2 is a 1% agarose electrophoretic gel showing detection of PCR products using oligonucleotide primers, QVR 137 and QVR 138, on an untreated control blood sample (Lane 4), blood sample seeded with approximately one *Salmonella* cell and enriched (Lane 3), blood sample with less than ten *Salmonella* cells (Lane 5), blood sample with approximately ten *Salmonella* cells (Lane 6) and blood sample with $10^3$ cells (Lane 7).

The assay was also performed by using isolated chromosomal DNA. For isolation of pure chromosomal DNA, the cultures were grown for 6 hr. in nutrient broth and DNA isolated by GES method (Pitcher et al., 1989). 10 ng of DNA was normally used in a 20 µl reaction assay Template preparation from blood: DNA isolation kit (M/S Bio Basic, Canada) was used for the isolation of DNA from blood. (FIG. 2).

Template preparation from water: For the isolation of DNA from water-borne bacteria, 1 ml of the sample was centrifuged at 7000 r.p.m for 3 min. in a 5 ml eppendorf tube, supernatant discarded and 10 µl of autoclaved Millipore water added to each tube. The resultant suspension was vortexed, incubated in a dry bath at 100° C. for 5 min. and the whole volume used in a 20 µl PCR reaction.

Enrichment: In case of blood 250 µl aliquots of the samples were inoculated into 5 ml liquid medium and for water 1 ml aliquots inoculated into 1 ml of double strength Brain Heart Infusion Broth (HiMedia, India) and incubated at 37° C. for 5 h. The cell lysates were prepared as above.

RESULTS

Oligonucleotide primers listed in Table 1 have been used to amplify PCR products from DNA template prepared from cultures of *Salmonella*. The oligonucleotide primers were designed to be complementary to regions of the *Salmonella* enterotoxin gene (stn) gene. FIG. 1 shows amplified products from primer set 1 (FIG. 1, Lane 2), primer set 2 (FIG. 1, Lane 3), primer set 3 (FIG. 1, Lane 4) and primer set 5 (FIG. 1, Lane 5). The sizes of the amplified products are approximately 200 bp, 207 bp, 1318 bp and 450 bp, respectively.

To show the efficiency of the method, varying numbers of *Salmonella* cells were inoculated into blood samples and used to prepare template DNA for the PCR reactions. FIG. 2 shows that PCR products were detectable in template DNA isolated from a blood sample having less than 10 cells (FIG. 2, Lane 5), blood sample having approximately 10 cells (FIG. 2, Lane 6), and blood sample having 10 cells (FIG. 2, Lane 7). Lane 4 shows a negative control and Lanes 2 and 3 are positive controls, with a DNA template isolated from blood sample inoculated with approximately one *Salmonella* cell and incubated for 5 hours in Lane 3. These results also demonstrate the ability to detect *Salmonella* in cultures of blood which may contain contaminating microflora in blood samples.

The method is highly specific and can detect as few as 1 cell per ml of water and as few as 10 cells per ml of blood without any pre-enrichment. The primers do not show any tendency to amplify non-*Salmonella* DNA. DNA from blood and background micro flora do not interfere with the PCR assay either by generating any non-specific PCR amplicons or by inhibiting the PCR assay.

Figure 3:
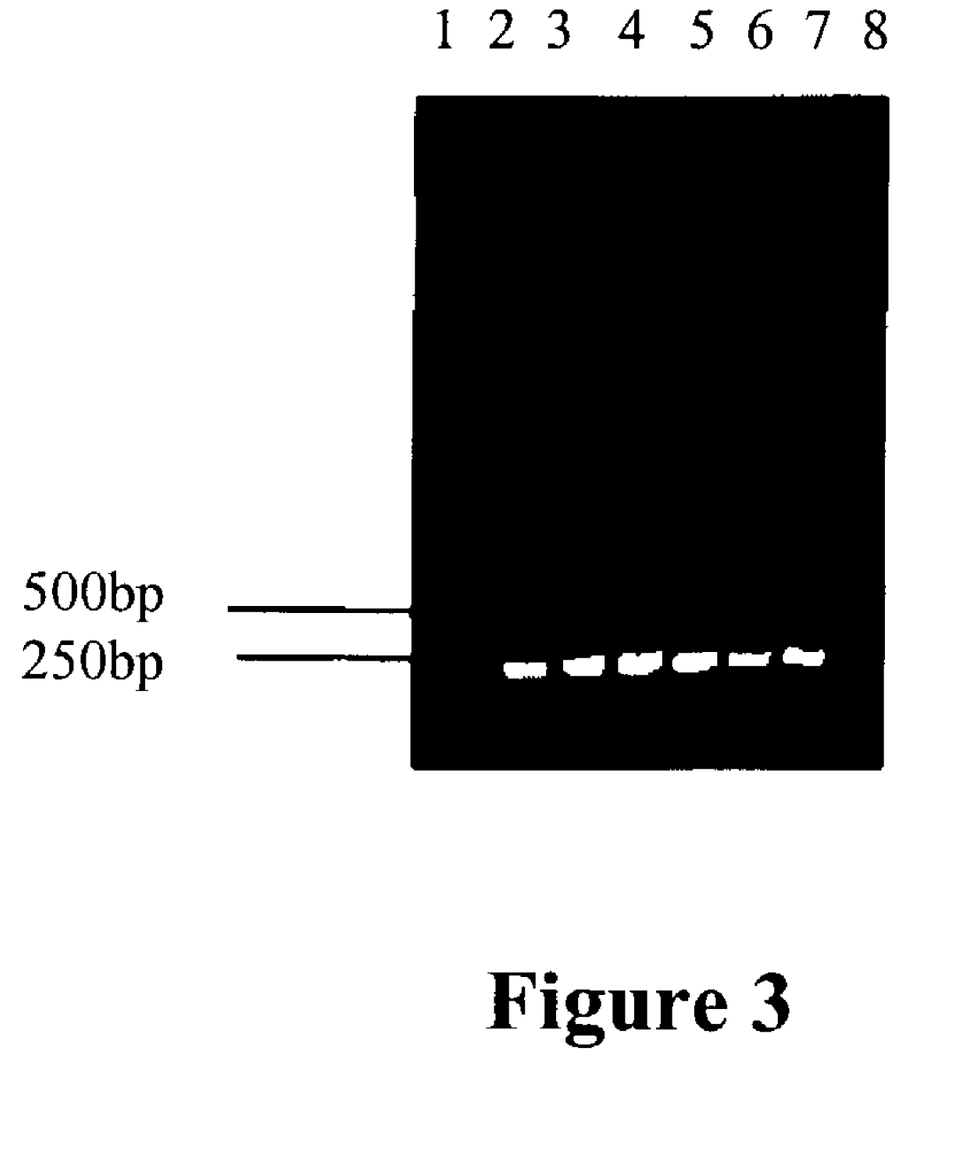
FIG. 3 is a 1% agarose electrophoretic gel showing detection of PCR products using nested PCR for using various serotypes of *Salmonella*. The first PCR reactions were run with primers, QVR137 and QVR138, and the second reaction was run with primers, QVR139 and QVR 140.

FIG. 3 shows that results of a nested PCR reaction using primer set 3, QVR137 and QVR138, followed by primer set 4, QVR139 and QVR140. The amplified PCR product is detected in all tested serotypes of *Salmonella* (Lanes 2–7).

We claim:

1. A method for the rapid and specific detection of one or more *Salmonella* cells in a sample using oligonucleotide primers selected from the group consisting of SEQ ID NOs. 1 to 10, comprising
    preparing a DNA template from the sample,
    amplifying the template with the oligonucleotide primers using polymerase chain reaction (PCR) to obtain PCR products,
    running the PCR products on an agarose gel, and
    detecting presence of *Salmonella* in the sample,
    wherein the presence of the PCR product is an indication of the presence of *Salmonella*,
    wherein the oligonucleotide primers are specific for the *Salmonella* stn gene.

2. The method of claim 1, wherein the stn gene is sequenced from various serotypes of *Salmonella*.

3. The method of claim 1, wherein the primers can detect as few as one *Salmonella* cell per ml of water.

4. The method of claim 1, wherein the primers can detect as few as ten *Salmonella* cells per ml of blood.

5. The method of claim 1, wherein the primers can detect as few as one cell per gram of food and clinical sample.

6. The method of claim 1, wherein DNA from blood and background micro flora does not interfere with PCR assay.

7. The method of claim 1, wherein the said method can be used as quality control of water and diagnosis of bacterium *Salmonella*.

8. The method of claim 1, wherein the sample is derived from the group consisting of humans and animals.

9. The method of claim 1, wherein the primers comprising SEQ ID NOs. 1 and 2 generates PCR products of approximately 200 bp.

10. The method of claim 1, wherein the primers comprising SEQ ID NOs. 3 and 4 generates PCR products of approximately 207 bp.

11. The method of claim 1, wherein the primers comprising SEQ ID NOs. 5 and 6 generates PCR products of approximately 1318 bp.

12. The method of claim 1, wherein the primers comprising SEQ ID NOs. 7 and 8 generates PCR products of approximately 450 bp.

13. The method of claim 1, wherein the primers is used in a concentration ranging between 1 pM to 100 pM.

14. The method of claim 1, wherein the agarose gel has a concentration ranging from 0.3% to 2.7%.

15. The method of claim 1, wherein PCR involves initial denaturation at a temperature of 93° C. to 97° C. for 30 sec. to 7 min, followed by 23 to 50 cycles of 93° C. to 97° C. for 3 sec. to 2 min for denaturation, 50° C. to 67° C. for 10 sec to 2 min. for annealing, 70° C. to 75° C. for 10 sec. to 2 min for extension, and followed by final extension at 70° C. to 75° C. for 2 min. to 10 min.

16. The method of claim 1, wherein the DNA is isolated from the group consisting of pure cultures, water, food and clinical samples.

* * * * *